(12) United States Patent
Engel et al.

(10) Patent No.: US 9,857,581 B2
(45) Date of Patent: Jan. 2, 2018

(54) LUMINESCENCE MICROSCOPY

(71) Applicant: Carl Zeiss Microscopy GmbH, Jena (DE)

(72) Inventors: Jorg Engel, Weida (DE); Thomas Kalkbrenner, Jena (DE); Wolfgang Bathe, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 177 days.

(21) Appl. No.: 14/893,240

(22) PCT Filed: May 27, 2014

(86) PCT No.: PCT/EP2014/060892
§ 371 (c)(1),
(2) Date: Nov. 23, 2015

(87) PCT Pub. No.: WO2014/191382
PCT Pub. Date: Dec. 4, 2014

(65) Prior Publication Data
US 2016/0116728 A1    Apr. 28, 2016

(30) Foreign Application Priority Data

May 28, 2013    (DE) .................. 10 2013 009 042

(51) Int. Cl.
*H04N 7/18*    (2006.01)
*G02B 21/36*    (2006.01)
(Continued)

(52) U.S. Cl.
CPC ....... *G02B 21/367* (2013.01); *G01N 21/6428* (2013.01); *G01N 21/6458* (2013.01);
(Continued)

(58) Field of Classification Search
CPC ...... G02B 21/16; G02B 21/367; G02B 27/58; G02B 21/26; G06T 2207/10056;
(Continued)

(56) References Cited

U.S. PATENT DOCUMENTS 7,675,045 B1 * 3/2010 Werner .............. G01N 21/6408
250/458.1
2010/0283835 A1    11/2010 Bewersdorf et al.
(Continued)

FOREIGN PATENT DOCUMENTS

DE    10 2008 009216 A1    8/2009
DE    10 2010 044013 A1    5/2012
DE    102010044013 A1 *    5/2012    ......... G01N 21/6428

OTHER PUBLICATIONS

Mlodzianoski, Michael J., et al.; "Sample drift correction in 3D fluorescence photoactivation localization microscopy"; Optics Express 2011; 19(16):15009-15019.
(Continued)

*Primary Examiner* — William Tran
(74) *Attorney, Agent, or Firm* — Duane Morris LLP

(57) ABSTRACT

The invention relates to a method for high-resolution luminescence microscopy of a specimen marked with marker molecules, and to a luminescence microscope for performing the method, wherein the marker molecules can be excited to emit luminescence radiation. The method for luminescence microscopy comprises the excitation and imaging of marker molecules and the transmission of a trigger time and a position of the specimen. An optical recording device images the marker molecules in a capture area and transmits data from the imaging to an image capture circuit. The recording device transmits a time for the imaging to a signal former as a trigger time; the trigger time is then transmitted to a data recorder. The data recorder generates a position of the specimen at the trigger time and (Continued)

transmits said position to the image capture circuit, which links the position of the specimen in the depth direction to the data of the imaging of a frame such that a three-dimensional tomographic image of the specimen can be created.

10 Claims, 2 Drawing Sheets

(51) Int. Cl.
  *G02B 21/16* (2006.01)
  *G02B 27/58* (2006.01)
  *G01N 21/64* (2006.01)
  *G02B 21/26* (2006.01)
  *G06T 7/77* (2017.01)
  *G06T 7/536* (2017.01)

(52) U.S. Cl.
  CPC ......... *G01N 21/6486* (2013.01); *G02B 21/16* (2013.01); *G02B 21/26* (2013.01); *G02B 27/58* (2013.01); *G06T 7/536* (2017.01); *G06T 7/77* (2017.01); *G06T 2200/04* (2013.01); *G06T 2207/10024* (2013.01); *G06T 2207/10056* (2013.01); *G06T 2207/10064* (2013.01); *G06T 2207/10072* (2013.01)

(58) Field of Classification Search
  CPC ....... G06T 2207/10024; G06T 2200/04; G06T 7/536; G06T 2207/10064; G06T 7/77; G06T 2207/10072; G01N 21/6486; G01N 21/6458; G01N 21/6428
  USPC .......................................................... 348/79
  See application file for complete search history.

(56) References Cited

U.S. PATENT DOCUMENTS

2011/0036996 A1    2/2011  Wolleschensky et al.
2013/0010098 A1*   1/2013  Kalkbrenner ...... G01N 21/6428
                                                    348/79

OTHER PUBLICATIONS

Notification of Transmittal of Translation, International Preliminary Report on Patentability, Written Opinion of the International Searching Authority.

* cited by examiner

LUMINESCENCE MICROSCOPY

RELATED APPLICATIONS

The present application is a U.S. National Stage application of International PCT Application No. PCT/EP2014/060892 filed on May 27, 2014 which claims priority benefit of German Application No. DE 10 2013 009 042.3 filed on May 28, 2013, the contents of each are incorporated by reference in their entirety.

FIELD OF THE INVENTION

The invention relates to a method for high-resolution luminescence microscopy of a specimen marked with marker molecules, where the marker molecules can be excited to emit luminescence radiation, and to a luminescence microscope.

BACKGROUND OF THE INVENTION

In luminescence microscopy, certain dyes such as phosphors or fluorophors are used for the specific marking of samples such as cell parts in the investigation of biological specimens. The sample is illuminated with illumination radiation representing an excitation radiation and the luminescence radiation excited in this way is picked up with detectors. For example, a beam splitter and block filter are provided for this in the microscope, which split the luminescence radiation from the excitation radiation and enable a separate observation. Thanks to this method, it is possible to represent individual, differently colored cell parts in the microscope. In multiple luminescence, several parts of a specimen are colored at the same time with different dyestuffs which bind specifically to different structures of the specimen. Moreover, one can survey samples which luminesce without adding dyes. Luminescence is being used here as a term covering phosphorescence and fluorescence.

Thus, it is known how to use marking molecules or a marking substance which can be activated by means of optical radiation. These marking molecules can only be excited in the activated state to emit certain luminescence radiation. Non-activated marking molecules even after exposed to excitation radiation emit no or at least no noticeable luminescence radiation. The activation radiation thus places the marking substance in a state in which it can be excited to luminesce. Other activation is also possible, such as thermal activation. The activation radiation is applied so that at least a certain fraction of the activated marking molecules are at a distance from neighboring activated molecules. After recording of the luminescence radiation, one then determines the center of their resolution-limited radiation distribution and from this determines mathematically the position of the molecules with high precision.

In luminescence microscopy, a position determination is performed with optical recording devices, such as highly sensitive cameras with a precision in the nanometer range. Various image evaluation methods are known for a localization of the marking molecules. But a high localization accuracy is only achieved laterally, i.e., in a plane coordinated with the image plane of the recording device. Thus, in this respect, the methods are limited to a two-dimensional analysis of the sample, and the plane is called, for example, the xy-plane.

For the localization of luminescent marking molecules in the third dimension, in the depth direction with respect to the imaging of the sample, designated as z for example, there are techniques known in the prior art. After the image recording of a layer, also known as a frame, the sample or an objective of the recording device is shifted in the depth direction in order to record another image of the next layer. The image recordings are then combined into a layer image comprising all the layers. In order to produce a layer image, each image recording must be tied in with the position of the sample in the depth direction.

A distance in the depth direction from one image recording to another should not be greater than a depth focus of the objective, also known as the capture region, for otherwise there will be gaps in the layer image. Therefore, a certain number of images have to be taken on account of the localization of the marking molecules in order to obtain a high-quality layer image.

An additional problem arises when making use of marking molecules. The excitation radiation or activation radiation is not confined to the image region of an individual image, that is, marking molecules are also excited or activated above and below the image region. These marking molecules are therefore not available for a further image recording in a higher or lower layer. The sample is bleached by the excitation radiation or activation radiation.

In order to reduce this effect, it has been proposed by Mlodzianoski et al., Optics Express 19, 15009 (2011) to shift the sample in the depth direction during a measurement process of many individual image recordings, while the sample is exposed to excitation radiation or activation radiation during the measurement. In this way, the bleaching of the sample is distributed over all layers of the overall measurement process.

Determining the position of the sample in the depth direction for each individual image recording is a major problem, since an overall time for the measurement cannot be extended by the position determination, on account of the bleaching of the sample. Furthermore, it must be possible to use any given positions in any given sequence in order to obtain a particular signal form of the position in the depth direction. Therefore, the basic problem which the present invention proposes to solve is to provide a method wherein image recording of a position of the sample is possible with any given position variation in the depth direction and without any delay.

SUMMARY OF THE INVENTION

The invention solves the problem by a method for luminescence microscopy which has an excitation and imaging of marking molecules, a transmission of a trigger time and a position of a sample at the trigger time according to claim 1. Further advantageous embodiments will emerge from the subclaims.

In the method for high-resolution luminescence microscopy of a sample, marking molecules such as synthetic dyes or fluorescent proteins are used, which can be stimulated to emit luminescence radiation or which are themselves luminescent. For the recording of an image of one layer of the sample, at first a partial quantity of the marking molecules present in the sample are excited to emit luminescence radiation, if they are not self-luminescent. The excitation can be done optically, for example, with the help of a laser, or thermally. It should be noted that the regions at least some of the time lie one behind another and partly overlap and that the regions are exposed in different manner to the radiation in terms of detection.

The radiation can be beamed in as a light sheet lying transverse to the depth direction. A shifting of the sample in the depth direction is preferably less than half the thickness of the light sheet. Alternatively, it is also possible to use two light sheets, lying such to each other than they overlap in the depth direction. A light sheet is the illumination which is beamed at an angle to the axis of detection, for example in the depth direction. As a rule, the illumination region comprises the region of a detection plane which is dictated by a detection optics. The illumination can be both parallel, e.g., produced by an anamorphotic optics, and sequential, produced by scanning with an excitation beam. A combination of the two variants is also possible.

In a next step, the marking molecules are imaged in a capture region by means of an optical recording device, such as a camera, and the imaging is transmitted to an image capture circuit, also known as a frame grabber.

The next step of the method involves transmission of a time of imaging of the marking molecules as a trigger time of the optical recording device to a signal former, also known as a signal shaper. The signal former saves the trigger time for later further processing and use. The signal former carries out any required processing of the trigger time into data or a data format.

After this, the trigger time is transmitted to a data recorder, which saves the trigger time for further processing. In the next step, a position of the sample in the depth direction or z-direction in relation to an objective of the optical recording device is transmitted to the data recorder.

In one advantageous embodiment of the method, before the transmission of the position of the sample in the depth direction a signal is generated by means of a signal generator in order to fix a vertical position of the sample and a particular position of the sample in relation to the objective is produced. For this, both the sample or the objective can be displaced.

Another advantageous configuration of the invention calls for the marking molecules to be activated so that they can only be excited to emit luminescence radiation after being activated, and an image recording furthermore has an activation of a partial quantity of the marking molecules present in the sample to emit luminescence radiation.

In an especially advantageous embodiment of the invention, the signal former sends a control signal to the signal generator to move to a vertical position. The control signal is preferably synchronized with the imaging of the marking molecules.

Another embodiment calls for the data recorder to determine by means of the trigger signal the position of the sample at the time of the imaging of the marking molecules and transmitting this to the image capture circuit, which brings together or links the imaging to the position.

In another advantageous embodiment of the invention, the trigger signal is used as a control signal for the excitation and/or activation of the marking molecules. This can be used in particular for a fading out, also known as blanking, of a lighting beam path, for example that of a laser. In one embodiment, the blanking of the lighting beam path is done during a reading time, for example a dead time of the optical recording device.

One embodiment of the invention calls for an actuator to control the vertical position of the sample and transmit the position of the sample at the time of the imaging of the marking molecules to the data recorder. The actuator is preferably designed as a piezoelectric actuator. In one advantageous embodiment, it is further specified that the controlling of a position of the sample is done during a reading time or dead time of the optical recording device. In another embodiment, the actuator positions either the sample or the objective of the optical recording device. What is important here is the relative position of the sample to the objective. In an especially advantageous embodiment, the actuator controls any desired sequence of positions, also known as a z-signal form. The positioning can be done continuously.

Of course, the above mentioned and yet to be explained features can be used not only in the indicated combinations, but also in other combinations or standing alone, without leaving the scope of the present invention.

Further features, details and benefits of the invention will emerge from the wording of the claims, as well as the description of sample embodiments with the aid of the figures.

BRIEF DESCRIPTION OF THE DRAWINGS

An embodiment of the invention shall be explained below in more detail with reference to the annexed drawings, in which.

DETAILED DESCRIPTION OF THE DRAWINGS

The reference numbers and their meaning are summarized in the following list of reference symbols. In general, the same reference numbers designate the same parts.

LIST OF REFERENCE SYMBOLS

Figure 1:
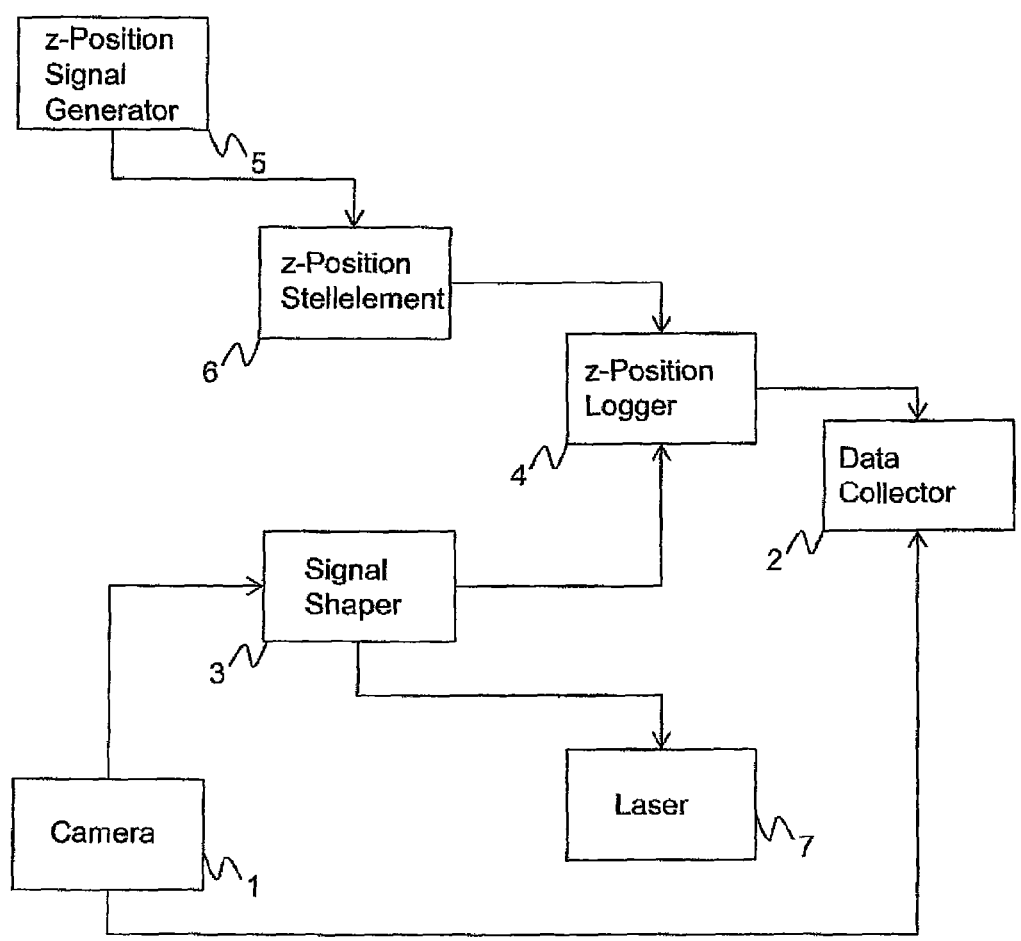
FIG. 1 is a schematic diagram of an image recording for luminescence microscopy.

1 Recording device
2 Image capture circuit
3 Signal former
4 Data recorder
5 Signal generator
6 Actuator
7 Laser FIG. 1 shows, in a schematic representation, the diagram of an image recording for luminescence microscopy. After the exciting of a partial quantity of the marking molecules present in the sample to emit luminescence radiation, an optical recording device 1 images the marking molecules in a capture region and transmits data of the imaging to an image capture circuit 2. The recording device 1 is in a free-run mode, for example, and the image recording is established by the recording device 1.

The recording device 1 transmits a time of imaging to a signal former 3 as the trigger time. After this, the trigger time is transmitted to the data recorder 4. The data recorder 4 determines by means of the trigger signal the position of the sample at the time of the imaging of the marking molecules and transmits the position to the image capture circuit 2. The data of the imaging are combined by the image capture circuit 2 with the position of the sample at the trigger time and thus yield a so-called frame or an image recording of a layer. After the conclusion of the measurement, these frames or layers are merged into a three-dimensional layer image of the sample.

The positioning of the sample in the depth direction or z-direction in relation to an objective of the optical recording device 1 is done by generating a signal to specify a vertical position of the sample by means of a signal generator 5. This is normally done once before the measurement of the sample, but it can also be done during the measurement and repeated as often as desired. During the measurement, after each layer a new position is moved to corresponding to the signal. An actuator 6 such as a piezoelectric actuator drives to the vertical position of the sample. Moreover, the position of the sample is preferably driven to by the actuator 6 in the reading time of the recording device 1. The actuator transmits the position of the sample at the time of the imaging of the marking molecules to the data recorder 4. The position of the sample at the time of the imaging of the marking molecules can also be transmitted additionally or exclusively by the signal generator 5 as a nominal signal in analog or digital form to the data recorder 4.

The actuator 6 controls any desired sequence of positions, for example, in a z-signal form. Any desired signal form can be chosen for this, such as periodic or stochastic. Moreover, the positioning of the sample by the actuator 6 can be done continuously. The actuator can additionally have an internal position sensor in order to generate an actual signal for the position of the sample in analog or digital form and transmit it additionally or exclusively to the data recorder 4.

Furthermore, the trigger signal of the recording device 1 can be used as a control signal for the excitation and/or activation of the marking molecules, for example, in order to control a fading or blanking of a lighting beam path of a laser 7. This blanking is moreover necessary in order to avoid needless bleaching of the sample. In event of bleaching of the sample, marking molecules above and below the image region are excited or activated. Thus, these marking molecules are no longer available for a further image recording in a higher or lower layer. Upon fading out or blanking of the laser 7, the laser signal is faded out as soon as the imaging of a layer is produced and the processing of the current data and a positioning process for the next layer is taking place.

Figure 2:
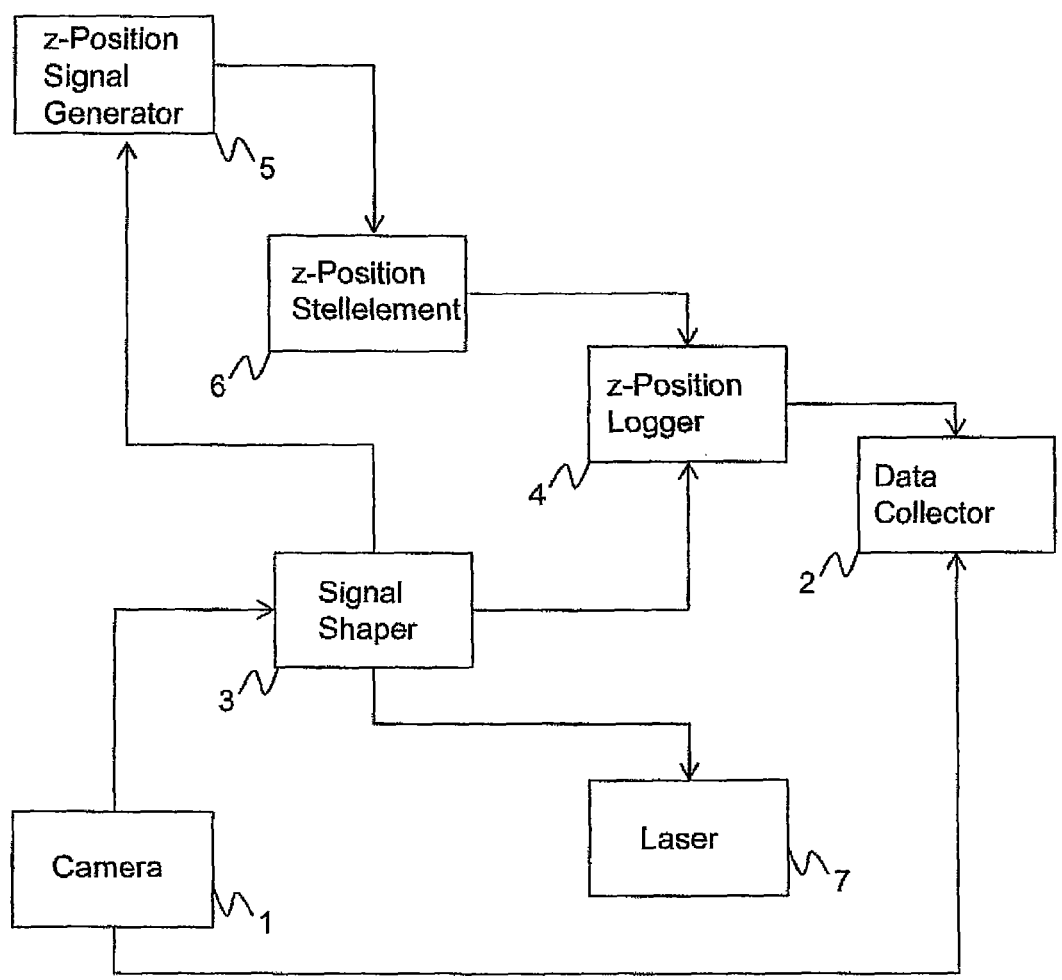
FIG. 2 is a schematic diagram of an image recording for luminescence microscopy with synchronous position generating.

FIG. 2 illustrates a method for synchronous position generating. The process here runs as in FIG. 1 with the difference that the positioning of the sample in the depth direction is triggered by the signal shaper 3. Thus, the positioning occurs synchronously with the image recording of the recording device 1, for example, by driving to a predefined list of positions.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for high-resolution luminescence microscopy of a specimen marked with marker molecules, where the marker molecules can be excited to emit luminescence radiation, and wherein image recording comprises the following steps:
    a) exciting a partial quantity of the marking molecules present in the sample to emit luminescence radiation;
    b) imaging the marking molecules in a capture region by means of an optical recording device and transmission of a time of the imaging of the marking molecules as a trigger time of the optical recording device to a signal former, wherein the trigger time is transmitted by the optical recording device;
    c) transmitting of the imaging to an image capture circuit;
    d) transmitting the trigger time from said signal former to a data recorder; and
    e) transmitting a position of the sample in a depth direction in relation to an objective of the optical recording device to the data recorder; and
    f) determining said position of the sample at the time of imaging of the marking molecule by means of the trigger time and transmitting said position of the sample to the image capture circuit, which brings together the imaging with the position, wherein a measurement of the sample has a plurality of image recordings and positionings, and the image recordings are merged together in combination with the position of the sample to form a layer image.

2. The method for high-resolution luminescence microscopy according to claim 1, further comprising positioning of the sample in the depth direction in relation to an objective of the optical recording device according to the following steps:
    generating a signal by means of a signal generator in order to fix a vertical position of the sample; and
    moving toward a position of the sample in relation to the objective.

3. The method for high-resolution luminescence microscopy according to claim 1, wherein the marking molecules are activated so that they can only be excited to emit luminescence radiation after being activated, and an image recording furthermore has the following step:
    activation of a partial quantity of the marking molecules present in the sample to emit luminescence radiation.

4. The method for high-resolution luminescence microscopy according to claim 2, wherein the signal former sends a control signal to the signal generator to move to a position in the depth direction, synchronized with the imaging of the marking molecules.

5. The method for high-resolution luminescence microscopy according to claim 1, wherein the trigger time is used as a control signal for the excitation and/or activation of the marking molecules, for a blanking of a lighting beam path.

6. The method for high-resolution luminescence microscopy according to claim 5, wherein the blanking of the lighting beam path occurs during a reading time of the optical recording device.

7. The method for high-resolution luminescence microscopy according to claim 6, wherein a piezoelectric actuator controls the vertical position of the sample and transmits the position of the sample at the time of imaging of the marking molecules to the data recorder.

8. The method for high-resolution luminescence microscopy according to claim 7, wherein controlling a position of the sample occurs during a reading time of the optical recording device.

9. The method for high-resolution luminescence microscopy according to claim 7, wherein the actuator positions the sample or the objective of the optical recording device.

10. The method for high-resolution luminescence microscopy according to claim 6, wherein the actuator controls any desired sequence of positions and the positioning is performed continuously.

* * * * *